(12) United States Patent
Sadeghian-Motahar et al.

(10) Patent No.: US 11,684,305 B2
(45) Date of Patent: Jun. 27, 2023

(54) ELECTRODE ARRAY CONFIGURATION ON A FLEXIBLE SUBSTRATE FOR ELECTRO-OCULOGRAM RECORDING

(71) Applicants: Seyedhesam Sadeghian-Motahar, Houston, TX (US); Jerald H. Simmons, Sugar Land, TX (US)

(72) Inventors: Seyedhesam Sadeghian-Motahar, Houston, TX (US); Jerald H. Simmons, Sugar Land, TX (US)

( * ) Notice: Subject to any disclaimer, the term of this patent is extended or adjusted under 35 U.S.C. 154(b) by 1060 days.

(21) Appl. No.: 16/429,052

(22) Filed: Jun. 2, 2019

(65) Prior Publication Data
US 2019/0365272 A1   Dec. 5, 2019

Related U.S. Application Data

(60) Provisional application No. 62/679,786, filed on Jun. 2, 2018.

(51) Int. Cl.
*A61B 5/398* (2021.01)
*A61B 5/00* (2006.01)

(52) U.S. Cl.
CPC ............ *A61B 5/398* (2021.01); *A61B 5/6821* (2013.01); *A61B 5/6832* (2013.01); *A61B 2562/125* (2013.01)

(58) Field of Classification Search
CPC ..... A61B 5/398; A61B 5/6821; A61B 5/6832; A61B 2562/125
See application file for complete search history.

(56) References Cited

U.S. PATENT DOCUMENTS

| | | | |
|---|---|---|---|
| 5,293,187 | A | 3/1994 | Knapp et al. |
| 5,360,971 | A | 11/1994 | Kaufman et al. |
| 5,491,492 | A | 2/1996 | Knapp et al. |
| 6,090,051 | A | 7/2000 | Marshall |
| 6,950,698 | B2 | 9/2005 | Sarkela |
| 7,197,357 | B2 | 3/2007 | Istvan et al. |

(Continued)

FOREIGN PATENT DOCUMENTS

| | | |
|---|---|---|
| CN | 103518172 A | 1/2014 |
| EP | 1493383 A2 | 1/2005 |

(Continued)

OTHER PUBLICATIONS

Heo J, Yoon H, Park KS. A Novel Wearable Forehead EOG Measurement System for Human Computer Interfaces. Sensors (Basel). Jun. 23, 2017;17(7). pii: E1485.

*Primary Examiner* — William R Alexander
*Assistant Examiner* — Sharrief I Broome
(74) *Attorney, Agent, or Firm* — Equip LG; Christopher Quan

(57) ABSTRACT

This invention is directed to a bio-potential electrode-set for measuring electrical signals during an electrooculogram (EOG) from a human, particularly to flexible self-adhesive bio-potential sensing electrode-set substrate specifically to cover the perimeter of the eyes for EOG recordings. In general, EOG is a technique for measuring the cornea-retinal standing potential that exists between the front and the back of the human eye. The resulting signal is called the electrooculogram. Primary applications include, but are not limited to, ophthalmological assessments that require recording eye movements or gaze tracking and human computer/machine interfaces.

12 Claims, 4 Drawing Sheets

(56) References Cited

U.S. PATENT DOCUMENTS

| | | | |
|---|---|---|---|
| 7,515,950 | B2 | 4/2009 | Healy |
| 8,434,868 | B2 | 5/2013 | Sato et al. |
| 8,473,024 | B2 | 6/2013 | Causevic et al. |
| 8,493,390 | B2 | 7/2013 | Kalinli |
| 8,739,397 | B2 | 6/2014 | Nagata |
| 9,095,268 | B2 | 8/2015 | Kurtz et al. |
| 9,211,075 | B2 | 12/2015 | Quintanar et al. |
| 9,579,060 | B1 | 2/2017 | Lisy et al. |
| 2008/0294066 | A1* | 11/2008 | Hetling ............ A61B 5/398 600/558 |
| 2009/0247894 | A1 | 10/2009 | Causevic |
| 2010/0041962 | A1* | 2/2010 | Causevic ............ A61B 5/377 600/383 |
| 2014/0257073 | A1* | 9/2014 | Machon ............ A61B 5/291 600/383 |
| 2014/0327609 | A1 | 11/2014 | Leroy et al. |
| 2015/0126845 | A1 | 5/2015 | Jin et al. |
| 2015/0238106 | A1 | 8/2015 | Lappalainen et al. |
| 2016/0228041 | A1* | 8/2016 | Heller ............ A61B 5/1473 |
| 2017/0143201 | A1* | 5/2017 | Claude ............ A61B 90/361 |
| 2017/0202491 | A1* | 7/2017 | Heller ............ A61B 5/14532 |
| 2018/0078165 | A1* | 3/2018 | Machon ............ A61B 5/6814 |
| 2019/0150775 | A1* | 5/2019 | Machon ............ A61B 5/6841 |

FOREIGN PATENT DOCUMENTS

| | | |
|---|---|---|
| EP | 2090225 A1 | 8/2009 |
| JP | 3287788 B2 | 6/2002 |
| KR | 101348233 B1 | 1/2014 |
| WO | WO2014131690 A1 | 2/2014 |

\* cited by examiner

ELECTRODE ARRAY CONFIGURATION ON A FLEXIBLE SUBSTRATE FOR ELECTRO-OCULOGRAM RECORDING

CROSS-REFERENCE TO RELATED APPLICATIONS

This application claims the benefit and priority of U.S. provisional patent application Ser. No. 62/679,786, filed Jun. 2, 2019, entitled "Flexible dense array bio-potential sensing electrode-set for Electro-oculogram recording", the contents of which is hereby incorporated by reference in its entirety.

FIELD OF THE INVENTION

The present invention relates to a method for fabricating and positioning electrodes in an electrode array on a self-adhesive flexible substrate comprising a plurality of electrodes for measuring electrical signals during an electro-oculogram, particularly for tracking the gaze position and movement of the human eye.

BACKGROUND OF THE INVENTION

Measuring movements of the eyes or gaze tracking with high accuracy is a desirable objective in many areas of research, clinical practice and for consumer devices for human computer/machine interfacing. In recent years, head mounted video-oculography (VOG) systems have been used for a diverse range of eye/gaze tracking purposes. However, these systems require wearing a head mounted camera system that may be uncomfortable and cumbersome to wear for long periods, are difficult to wear along with corrective lenses, and not suitable for all recording environments. Additionally, they require a stable relationship with the head. Any abrupt movement of the head cameras that alters this fixed relationship introduces artifact. Any fogging of the camera lens can also alter the data. An alternative method of recording gaze and eye tracking movements is referred to as the electro-oculogram (EOG) which measures the measures electro-potential difference between the retina and the cornea which can be modeled as a dipole for each eyeball with the cornea having the positive end and the retina having the negative end of the dipole. The discrete nature of the EOG recording apparatus allows the subject to wear corrective lenses if necessary, or to use a head-mounted visual stimulus delivery system such as virtual reality goggles without obstruction. Plus there are some applications that are in the exclusive domain of EOG such as a component of sleep testing, biofeedback, and during electroencephalogram (EEG) testing.

Another limitation of the VOG is the sampling rate afforded by most systems, typically from 30-60 Hz, VOG is a trade-off between high spatial resolution and weaker temporal frequency. EOG can be sampled at a significantly higher frequency, beyond 1000 Hz, depending on the amplified sampling rate. Thus EOG is the method of choice in conditions requiring fast sampling rate, for example, analyzing saccade eye movements or identifying early stages of oculomotor pathology in certain neurologic conditions.

U.S. Pat. No. 6,950,698 discloses an electrode array comprising at least four measurement electrodes positioned on the forehead and possibly also in the temple area of the patient. The drawback with this and most current EOG electrode configuration is that they perform eye movement assessment using few number of electrodes placed in a horizontal axis combining the electrical fields of both eyes with electrodes placed on the lateral aspects of the head and measure the vertical movements from just one eye with electrodes placed above and below one of the eyes. This technique is not adequate to assess vergence eye movements, such as convergence in which each eye rotates inward to fixate on an object that are in close proximity, such as right in front of the nose. Convergence testing is one of the most sensitive measures when assessing for eye movement abnormalities, such as those following a concussion. In order to use EOG to assess convergence abnormalities, each eye must be assessed independently. Hence an electrode array configuration that includes medial measurements is required, with electrodes placed by the bridge of the nose bilaterally as cited in Furman et al,. 2012 a minimum of 7 electrodes is required. However, such testing using standard electrode systems is extremely bulky and not practical for frequent large scale usage.

U.S. Pat. No. 5,293,187 by Knapp, 1994, describes an EOG system that utilizes a series of electrodes within a band around the forehead for the measurement of horizontal eye movements to characterize convergence and strabismus eye movements. However, this system does not provide vertical eye measurements and cannot be used for eye tracking to determine the exact gaze of a subject.

Unfortunately, the current conventional electrodes for measuring EOG are cumbersome as they require individual placement of each electrode, hence limited in the number of electrodes that can be practically applied around the eyes, eyebrows and nose. They are impractical in most settings that require quick application of an EOG electrode-array. Positioning an array or plurality of connectional electrodes for EOG recording is cumbersome and impractical because conventional electrodes are typically made out of metal (e.g. brass, gold or tin) connected to metal leads. The conventional electrodes (metal based) are not flexible to conform to the facial curvature such as the bones around the eyes/eyebrows and nose. Placing an array of the conventional electrodes around the eyes while maintaining good contact with the skin is very challenging and cumbersome since they connect to an amplifier via wires, resulting in many leads or wires attached on subject's face which can cause discomfort, especially in prolonged recording, reduces compliance and thus limits the practical utilization of EOG signal recording on a routine basis in a wider capacity.

Another type of electrodes widely used for EOG are pre-gelled self-adhesive EMG/EKG electrodes, but these electrodes have a large foot print and require individual placement of each electrode, which limits the number of electrodes that can be practically applied around the eyes and/or eye brows and/or nose, and is impractical in in many settings that require quick electrode application. Therefore, typical electrode configuration measuring EOG usually consist of only 4 to 6 electrodes covering both eyes (FIG. 2) and do not provide monocular assessments simultaneously for each eye.

U.S. Pat. No. 8,473,024, U.S. Patent Publications US20150238106A1 and US20100041962A1, European patent application EP2090225A1 and Korean patent KR101348233B1 describe systems with few EOG electrode sight and configuration around the eyes, eyebrows and inherit the limited accuracy discussed above.

SUMMARY OF THE INVENTION

The present invention relates to a method for fabricating and positioning electrodes in an electrode array on a self-adhesive flexible substrate comprising a plurality of electrodes for measuring electrical signals during electro-oculograms (EOG), particularly for tracking the gaze position and movement of the human eye.

The present invention provides an electrode configuration method and an electrode array for EOG monitoring from around the eyes, eyebrows and nose of a subject. Aspects of the present invention provide a method and an electrode array around the eyes, to enable more EOG data sources to be analyzed. Higher number of electrodes around the eyes provide greater opportunity for adequate spatial sampling of eye electrical events so that both vertical and horizontal eye movements are dealt with better accuracy.

Positioning of a plurality of bio-potential electrodes on a flexible substrate offers two significant technical advantages. First, flexible substrate will conform to the facial contours around the orbit of the eye, whereas conventional electrodes come short. Secondly, a plurality of bio-potential electrodes improve the signal-to-noise ratio measured from EOG due to the many sensors encompassing eyes (plurality) as opposed to few, which results in higher sensitivity to vertical and horizontal gaze-eye movement, hence improved overall eye-gaze tracking estimation.

Placement of an array or plurality of conventional electrodes for EOG recording is challenging and impractical for prolonged recording. Because such conventional electrodes are metal based (gold or brass typically) and connect to an amplifier via wires resulting in many leads or wires on a subject's face causes discomfort, is cumbersome, especially in prolonged recording, reduces compliance and thus limits the practical utilization of EOG signal recording on a routine basis in a wider capacity. Another type of electrodes widely used for EOG are pre-gelled EMG/EKG electrodes that are placed around the eyes, but these electrodes have a large foot print and require individual placement of each electrode, which limits the number of electrodes that can be practically applied around the eyes and/or eye brows and/or nose and is impractical in in many settings that require quick electrode application. Hence conventional electrodes, pre-gelled or not, are not a practical solution for routine EOG recordings on a large scale.

In general, the self-adhesive flexible EOG electrode-set disclosed herein includes electrodes and leads fabricated on a flexible substrate such as plastic, flexible polymer films, paper, foil or other similar materials, such as, for example, having a thickness of less 0.01 inches, that will conform well to the facial curvature around the eyes, eyebrows and nose, to make good contact with the skin.

In some exemplary embodiments, the electrodes are fabricated directly onto the surface of a flexible substrate from depositing conductive ink, such as metal-based ink or conductive organic ink, such as poly(3,4-ethylenedioxythiophene) polystyrene sulfonate (PEDOT:PSS), in a shape to create a perimeter that conforms around each eye. In general, the substrate may utilize an adhesive backing layer to be peeled off to adhere the electrode-array substrate on the skin around the eye of a subject, so the electrode-set substrate, consisting of two or more electrode contacts, can stick to the skin around the perimeter of the eyes. In general, the electrode set may be utilized, with an appropriate EOG amplifier system to record and analyze EOG signals from many locations around the eyes/eye brows/nose/forehead, as opposed to the typical few (e.g. 4 or 6) electrodes when using conventional electrodes, to improve overall eye-gaze and movement direction tracking, thus increasing the accuracy of eye or gaze tracking analyses.

The present invention together with the above and other advantages may best be understood from the following detailed description of the embodiments of the invention illustrated in the drawings.

DETAILED DESCRIPTION OF THE INVENTION

The detailed description set forth below is intended as a description of the presently exemplified devices, methods and materials provided in accordance with aspects of the present invention, and it is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates to a method for fabricating and positioning electrodes in an electrode array on a self-adhesive flexible substrate comprising a plurality of electrodes for measuring electrical signals during an electro-oculogram (EOG), particularly for tracking the gaze position and movement of the human eye.

Figure 1:
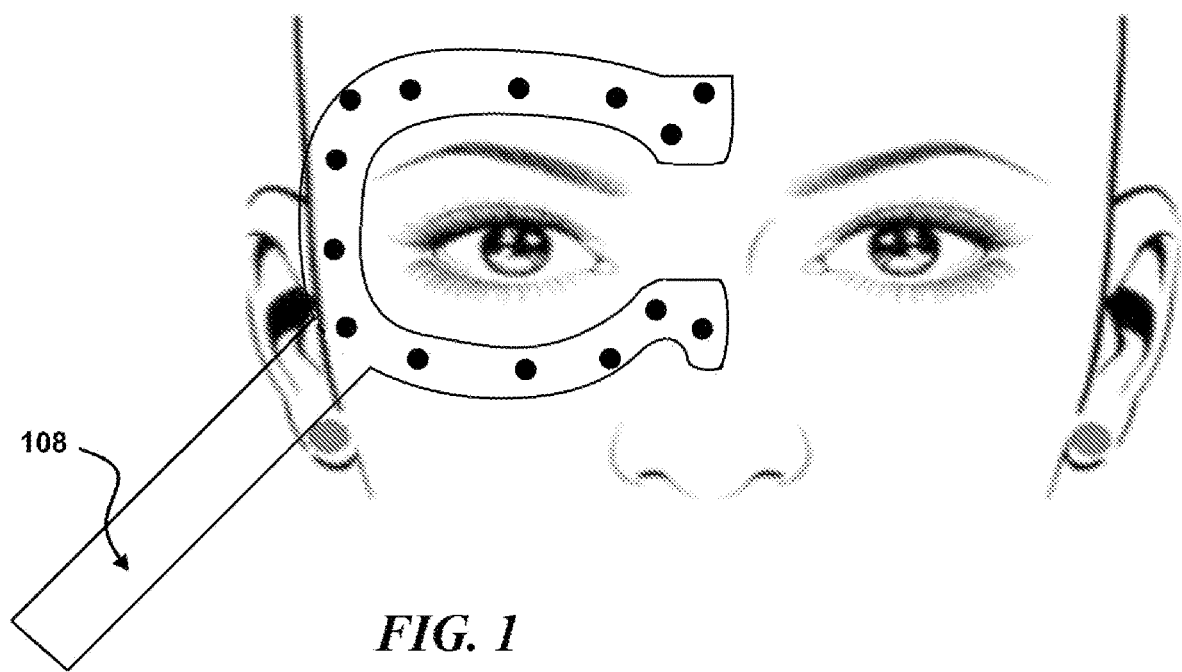
FIG. 1 illustrates an embodiment of the invention with a 14-channel electrode array configuration conforming the perimeter of the right eye.
Figure 2:
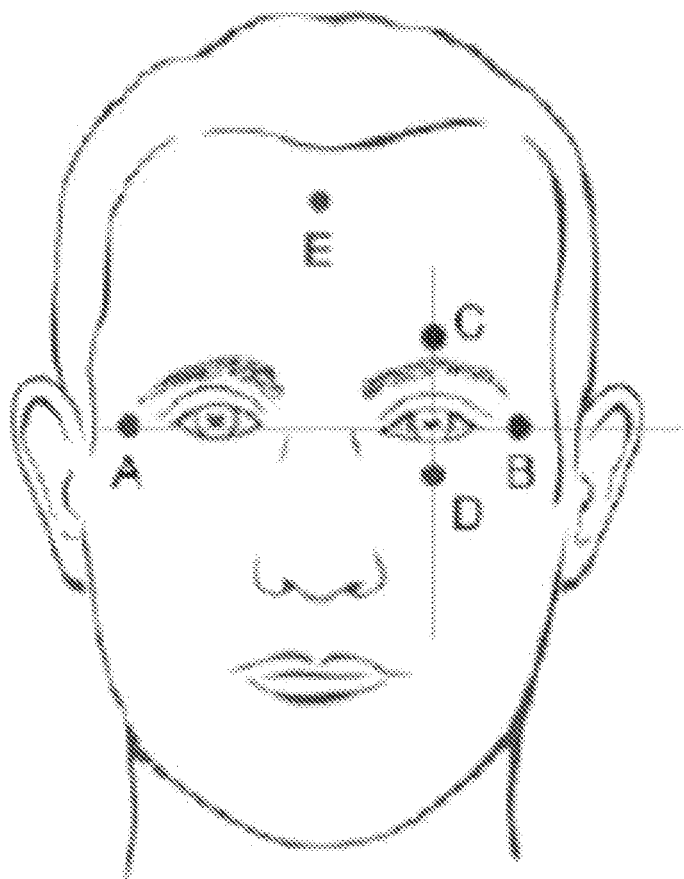
FIG. 2 is a frontal view of a human head illustrating a prior art EOG electrode placement for detecting eye movements where electrodes at locations A, B measures eyes' horizontal and C, D measures eyes' vertical movements.

FIG. 1 illustrates an embodiment of the electrode-array configuration of the invention conforming the perimeter of the right eye such as above eyebrow, around and side of the eye and nose for measuring the EOG signal as opposed to a few electrodes used in prior art technique for detecting eye movements, as illustrated with a 14-channel configuration (FIG. 2). The drawback with prior art EOG electrode configurations (FIG. 2) is that they perform eye movement assessment using few number of electrodes placed in a horizontal axis (points A, B of FIG. 2) combining the electrical fields of both eyes with electrodes placed on the lateral aspects of the head and measure the vertical movements from just one eye with electrodes placed above and below one of the eyes (points C, B of FIG. 2). This technique is not adequate to assess vergence eye movements, such as convergence in which each eye rotates inward to fixate on an object that are in close proximity, such as right in front of the nose. Convergence testing is one of the most sensitive measures when assessing for eye movement abnormalities, such as those following a concussion. In order to use EOG to assess convergence abnormalities, each eye must be assessed independently as cited in Furman et al,. 2012. Hence the electrode array configuration disclosed herein includes medial measurements with electrodes placed by the bridge of the nose bilaterally.

Figure 3:
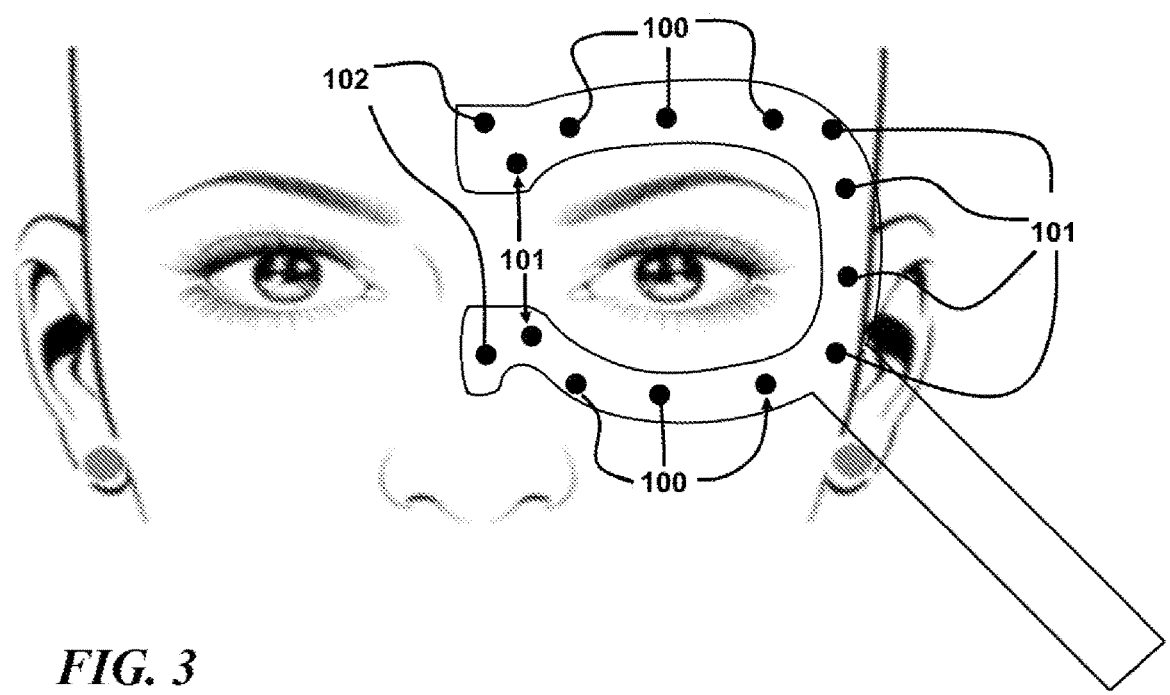
FIG. 3 illustrates one embodiment of the 14-channel electrode-array on a flexible substrate with plurality of electrodes positioned horizontally at roughly equal distance as illustrated as 100 in FIG. 3 to pick up electrical signals caused by vertical eye movements, and group of electrodes positioned to the side and corner of the eye 101 to remain sensitive to the eye movement in the horizontal direction, electrode positions for a ground electrode (GND) providing a common ground potential (0V) for the channels, and a reference electrode 102 which the EOG signals are measured against.

FIG. 3 illustrates one embodiment of the electrode array on a flexible substrate with plurality of electrodes 100 positioned horizontally at roughly equal distance from each other onto the hairless frontal lobe of the subject above the eyebrows and beneath the eye as illustrated in FIG. 3 to pick up electrical signals caused by vertical eye movements, and a group of electrodes 101 positioned to the side and by the bridge of the nose bilaterally to remain sensitive to the eye movement in the horizontal direction allowing more accurate detection of the potential changes caused by horizontal eye movements. The configuration may further include electrode positions for a ground electrode 102 (GND) providing a common ground potential (0V) for the channels, and a reference electrode 102 which the EOG signals are measured against, as illustrated in FIG. 3. The reference electrode may also be any of the electrodes or be positioned at behind the left ear mastoid or right ear mastoid.

In some exemplary embodiments, the EOG electrode-array above the eyebrows as shown in 100 of FIG. 3 may also be used to record combined electroencephalogram (EEG)/EOG signals to be analyzed for characterization of sleep stages.

Figure 4:
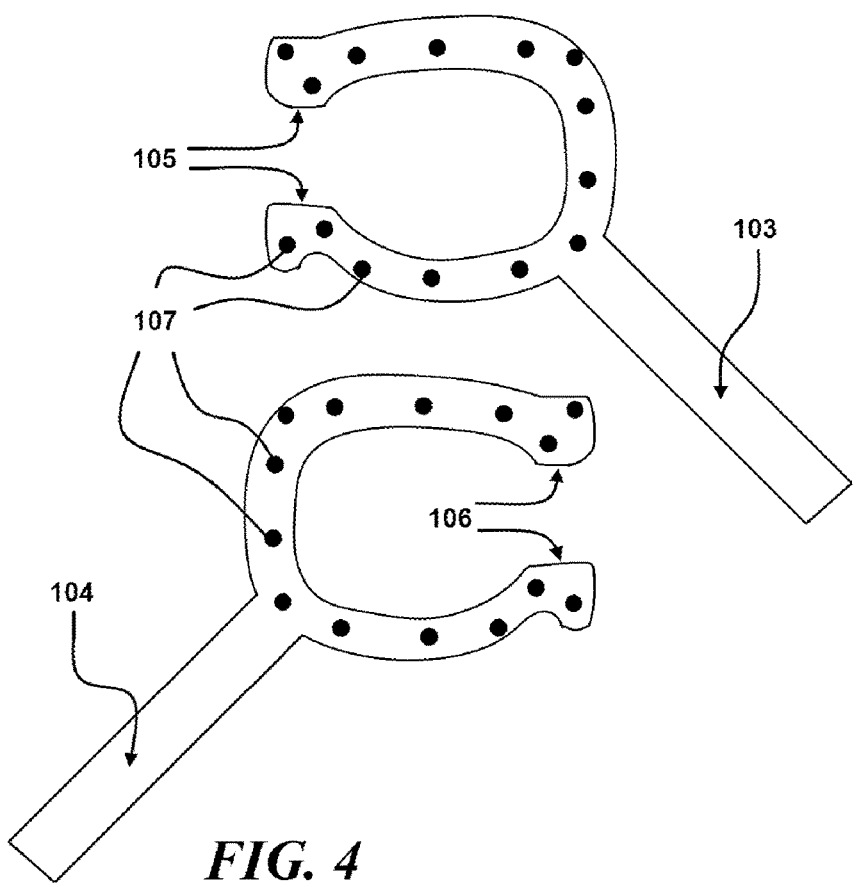
FIG. 4 illustrates two embodiments of the electrode-array fabricated and positioned on a self-adhesive flexible Bemis adhesive thermoplastic polyurethane (TPU) substrate cut in a shape of C to conform to the perimeter of the left eye 103 and right eye 104 and to allow the jaw as illustrated as 105, 106 to slightly close or open to conform all the configured electrodes 107 to various eye sizes.

FIG. 4 illustrates two embodiments of the electrode array fabricated and positioned on a self-adhesive flexible Bemis adhesive thermoplastic polyurethane (TPU) substrate cut or formed in a shape of C to conform to the perimeter of the left eye, as illustrated with array 103, and the right eye, as illustrated with array 104. The C shape allows the jaw 105, 106 to slightly close or open to conform the configured electrodes 107 to various eye sizes. The substrate that encompassed the right and left eye are symmetrical to one another with symmetrical positions of the electrodes (FIG. 4).

In some exemplary embodiments, the electrode-array may be fabricated directly onto the flexible substrate via deposition of conductive ink onto a flexible substrate in a C-like shape (e.g. C-shaped, horseshoe-shaped, etc.) that conforms the perimeter of the eye to be placed in contact with the human face on the skin as shown in FIG. 1 and FIG. 3, to receive bio-potential signals from the human eye movements. For example, the EOG electrode array electrodes 100, 101, 102 and along with conductive traces 111 may be screen-printed or inkjet-printed on the flexible substrate 108 using a conductive metal ink such as silver (Ag) ink or, silver-silver chloride (Ag—AgCl) ink to conduct electrical signals resulting from human eye movements.

Other example of conductive ink used to fabricate the electrode array may be organic conductive ink such as poly(3,4-ethylenedioxythiophene) polystyrene sulfonate (PEDOT:PSS), or conductive graphene or carbon based ink.

In some exemplary embodiments, an insulating layer is placed over the conductive traces 111 and not over the electrode areas 107 such that the electrodes may still contact the skin and the conductive traces are protected and/or insulated from electrical signals and/or from short circuit. The insulating layer may be fabricated using deposition of dielectric ink with screen-printing machine or ink-jet printing method using an inkjet printer. The electrode array electrodes 100, 101, 102 may come in contact with the face on the skin around the perimeter of the eyes and conductively linked by the conductive traces 111 to a connection point 112.

Figure 5:
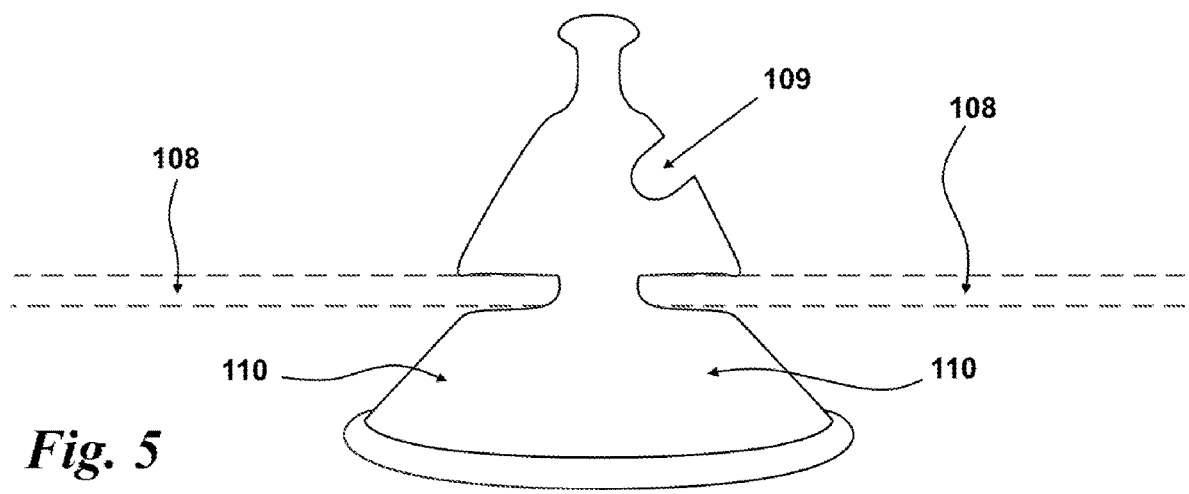
FIG. 5 illustrates an example of a harness assembly at the electrode sites with a cavity 110 that is filled from a small hole 109 with conductive fluid or EEG gel reservoirs to allow passage of electrical signals resulting from eye movement to the conductive traces fabricated on the substrate 108.

In some exemplary embodiments, as illustrated in FIG. 5, a conductive polymer-based cavity 110 may be assembled at electrode sites and may get filled with an amount of a conductive fluid, gel, paste or similar substance, such as, for example, silver-silver chloride (Ag—AgCl) cream such as conductive Ten20 paste or similar conductive EEG paste through the hole in the cavity 109 to lower the skin-to-contact impedance to improve the signal to noise ratio.

In some exemplary embodiments, the substrate 108 may be glued to an adhesive polymer or foam layer such as 3M Medical Adhesive film tape or TPU so that the backing layer can be peeled off to adhere the electrode-array substrate directly onto the face around the eyes.

In some exemplary embodiments, the flexible substrate 108 used to fabricate the electrode-array may be polymer films or sheets, such as polyethylene, polyethylene terephthalate (PET) or variations such as biaxially oriented PET (BoPET), polypropylene, polyimide, Extend film, polyethylene-naphthalate, fluorinated polymers (e.g. PTFE, PFA, FEP, etc.) polyester, silicone, polyurethane, or vinyl; paper; foils; medical foam; heat-fusion TPU, rubbers and/or any other appropriate material or combination thereof.

In some exemplary embodiments, the substrate may utilize an adhesive backing-layer that can be peeled off to adhere the electrode-array substrate on the skin around the eye of a subject. so that the electrode-substrate can stick onto the face so the electrodes can encompass the eyes and make good contact with the skin. In general, the electrode-set may be utilized with an appropriate EOG system to record EOG signals from many sources or locations around the eyes/eye brows/nose/forehead to improve eye-gaze tracking direction and angle.

In some exemplary embodiments, the flexible EOG electrode-set consists of an array of electrodes being deposited using a conductive ink on a flexible substrate cut or formed in a substantially C-like shape to conform to the perimeter of the eyes using a die-cutter machine or laser cutter. The open jaw of the C-shaped substrate 105, 106, as illustrated in FIG. 4, may, for example, be utilized such that the jaw can slightly open further or close in to adjust to various eye perimeter sizes.

Figure 6:
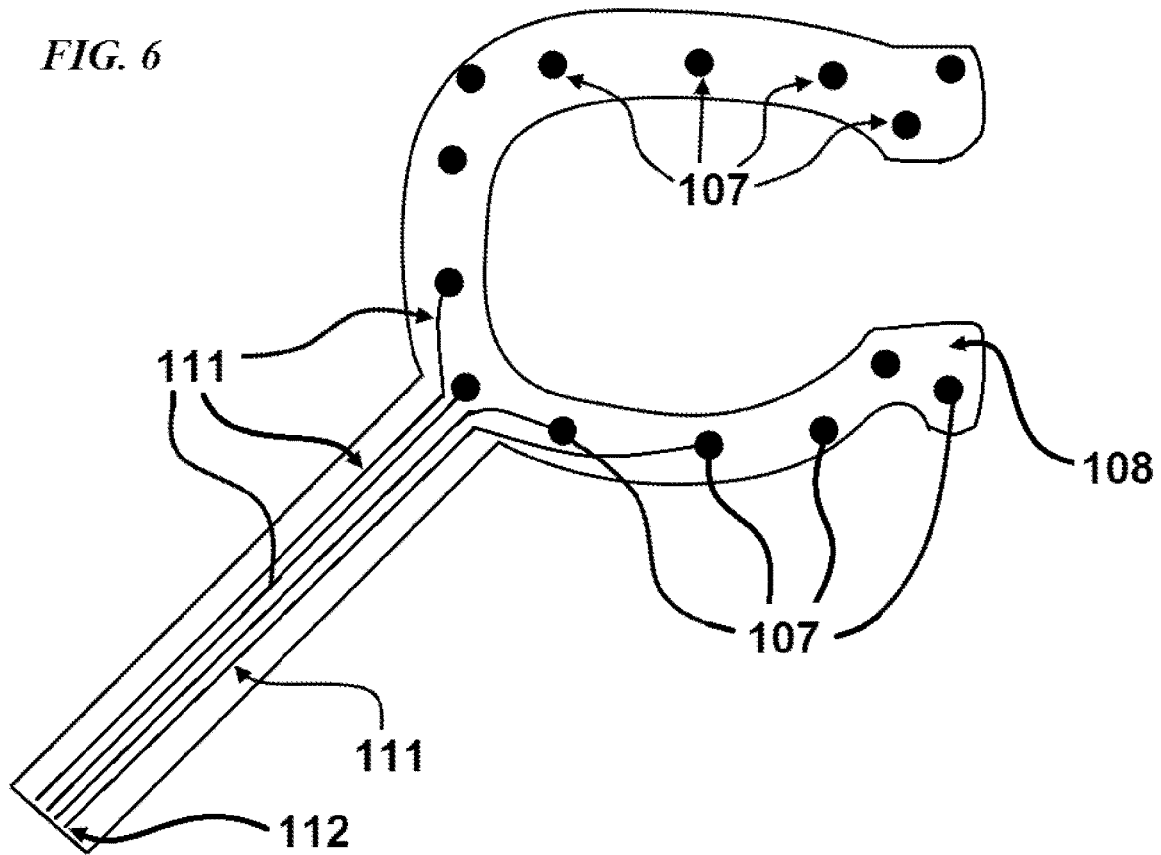
FIG. 6 illustrates one embodiment of the electrode array showing the conductive traces 111 that are directly fabricated onto a flexible polyethylene terephthalate (PET) substrate to route the electrical signals resulting from eye movement at the electrode sites 107 toward the end of the substrate where it meets the connector.

In an exemplary embodiment, the flexible EOG electrode-set may be fabricated via screen-printing (silk-printing) or ink-jet printing conductive metal ink (such as silver ink or silver-chloride ink) onto flexible substrates 108 to create conductive traces 111 connected to electrodes 107. Each conductive trace 111 is connected to each electrode 107. Conductive traces are separated by a distance from each other to avoid short circuit or cross-talk, as illustrated in FIG. 6. Subsequently, a protective substance, such as an insulating or dielectric ink, may be deposited, such as by using screen-printing or ink-jet printing dielectric or insulting ink, over the conductive traces to act as an insulating layer except for at the electrodes 107. This protective substance may also be sprayed for example using a Siphon or gravity-based air-brush. Additional items or features, such as insulating or protective layers, adhesives foams or layers, electrode cream such as EEG silver, Ag—AgCl gel or other enhancing backing layers may also be applied to the substrate 108. Following this step, the substrate may be cut using die-cutting machine or laser cutter in a C-shape that encompasses the eyes.

Figure 9:
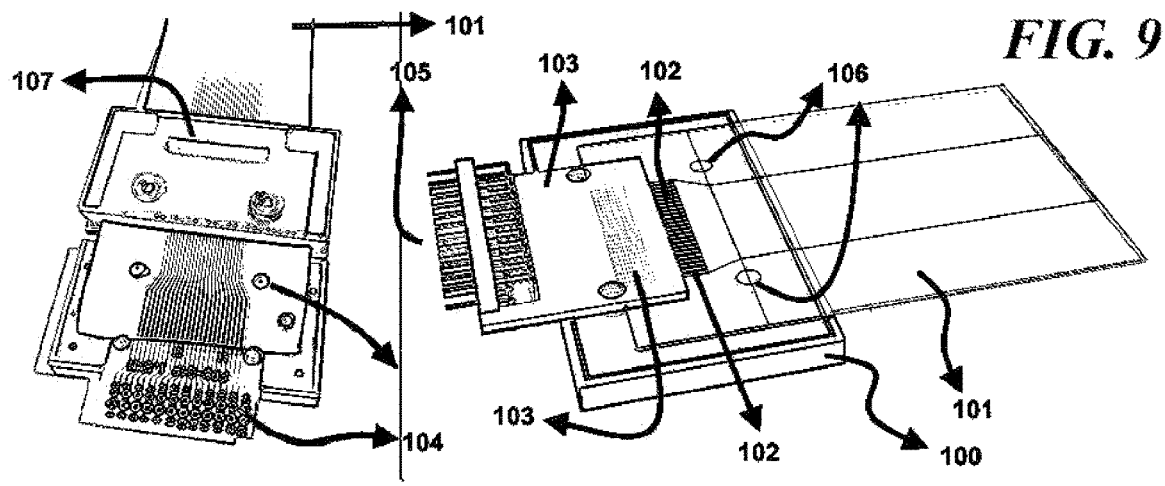
FIG. 9 illustrates one embodiment of the respective connector 118 with a mechanism to hold the substrate 108 in place by punching holes with certain diameter in certain position 123 on the substrate and making rods 124 on the connector with same diameter and certain position such that when substrate is placed over the connector, conductive traces at the end the strip-like lines 112 will be aligned with the traces 119 of the printed circuit board 120 connected to right angled pins 121, that is connected to the cable (not shown) connecting to the amplifier state of the art measuring EOG signals. The connector 118 may further include a cap or cover 125 to hold the configuration in place.

In some exemplary embodiments, the flexible EOG electrode array may include contacts at the tail 112 of the electrode array, such as crimped into the substrate, as shown in FIG. 9. The contacts may be male or female with 1.0 millimeter or 1.27 millimeter or 2.54 millimeter pitch (distance from center of one trace to another at the connector end) with or without connector housing. The connector 118 may include a mechanism to hold the substrate 108 in place, such as by punching holes with certain diameter in certain position 123 on the substrate and passing through rods 124 on the connector with same diameter and certain position such that when substrate is placed over the connector, the conductive traces at the end of the substrate 112 are aligned with the traces 119 of the printed circuit board 120 which through right angled pins 121, that is connected to the cable (not shown) connecting to the amplifier or other signal processor/receiver measuring EOG signals.

Example of EOG Preliminary Data

Figure 7:
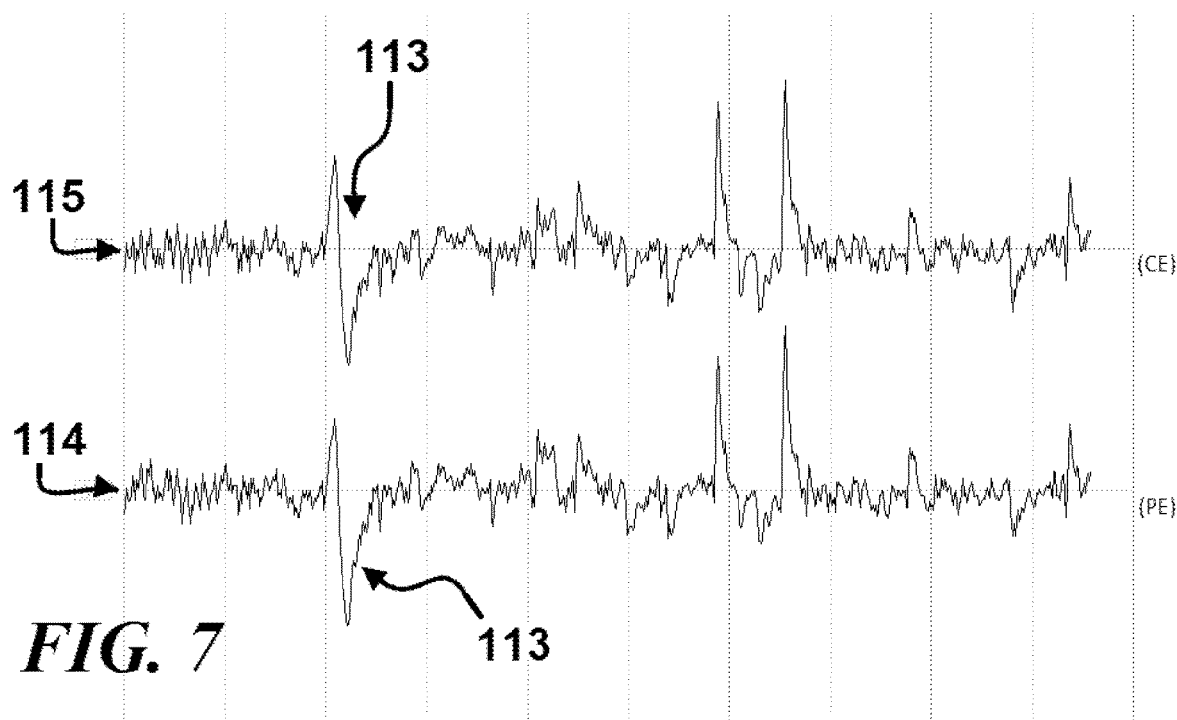
FIG. 7 illustrates blink data 113 comprising eye-close and eye-open movement, measured at location on forehead above eyebrows near FP1 on a human subject contrasting the performance of the flexible EOG electrode-array 114 to that of conventional electrode 115.
Figure 8:
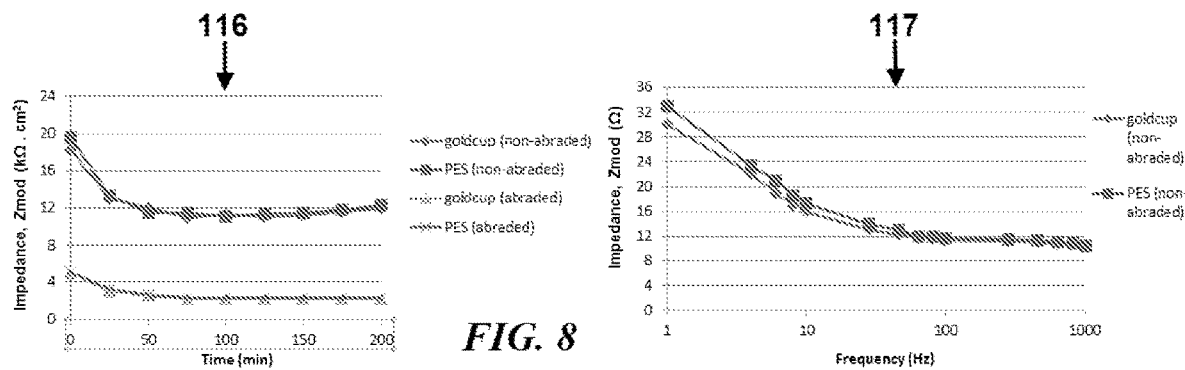
FIG. 8 illustrates one skin-to-contact function of impedance change over time at 30 Hz frequency 116, and another skin-to-contact function of impedance change at various frequencies 117, contrasting the performance of flexible EOG electrode-array to that of conventional electrode (labeled as goldcup)

As preliminary means to compare the performance of the flexible EOG electrode array to conventional EEG electrodes (gold discs with Ten20 conductive paste), simple EEG recording was performed as a proof-of-concept, contrasting the performance of flexible EOG electrode array, as shown with the signal output 114, against that of goldcup electrode (used in clinic as gold standard), as illustrated with the signal output 115 of FIG. 7. EOG was recorded using microEEG amplifier with a 500 Hz sampling frequency, a hardware bandpass filter of 0.1-100 Hz, notch-filter and 0.5 μV amplitude resolution. The presence of open/closing eyes (blink) 113 was observed and compared in the EOG signals. Impedance spectroscopy is often used to study the electrode-skin interface. For this experiment, the impedance between the gold clinical standard electrode and counter EOG electrode was measured on human scalp with potentiostatic EIS using a Gamry FAS2 Femtostat. Array. Qualitative comparison using time-domain 116 and frequency response curve 117 as illustrated in FIG. 8 for each channel and across subjects indicated comparable performance between flexible EOG electrode-array and the gold standard disc electrode, with similar features of eye movements and eye blinks observed in both recordings.

Example of Fabrication of Electrode-Set or Headpiece

A 14-channel electrode array was screen-printed printed on a flexible A4 size TPU with ground and reference electrodes 102 as illustrated in FIG. 3. The printed side of the flexible substrate sheet was then screen-printed using a dielectric ink acting as an insulating layer, with the electrode sites left uncovered such that the electrodes may come in contact with the skin, as illustrated with electrodes 100 and 101 in FIG. 3. The printed side of the electrode-array are backed with self-adhesive layer, which consists of a double sided medical foam with thicknesses between 0.5 mm to 5 mm, this foam has a hole (cavity) at electrode-sites that is filled with EEG ionic gel such as Ag—AgCl or sodium chloride (NaCl) to allow passage of biosensing signals from the scalp to the printed conductive traces. The electrode-array is applied by peeling off the adhesive backing layer and adhering to a subject's face around the eye. The screen-jet printed electrode-array was cut using die-cutting machine in a shape of C to conform to the facial contours around the orbit of the eye.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", "an exemplary embodiment" or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", "in some embodiments" or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a suitable amplifier coupled with a software via a Bluetooth or network (for example, the Internet), another computer, or in a standalone computer. As is known to those skilled in the art, a suitable amplifier system a can include a front-end analog to digital unit, at least one micro-controller, at least one Bluetooth or Micro-SD card, and one or more input/output ("I/O") device(s). The I/O devices can include inputs from an event trigger device or other sensors.

Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. An electrode array for use in electro-oculography comprising:
   a flexible substrate formed from a non-electrically conductive material, said flexible substrate comprising a C-shaped portion and a connector portion;
   a plurality of electrodes at predetermined locations on said C-shaped portion, said plurality of electrodes comprising a set of measurement electrodes, at least one ground electrode and a reference electrode, said at least one ground electrode providing a common ground potential of 0 Volts for said measurement electrodes; and
   a plurality of conductive traces connecting said plurality of electrodes to said connector portion;
   wherein said C-shaped portion is sized and shaped to conform and substantially circumscribe a human eye orbit.

2. The electrode array of claim 1, wherein said non-electrically conductive material is selected from the group consisting of polyethylene, polyethylene terephthalate (PET), biaxially oriented PET (BoPET), polypropylene, polyimide, Extend film, polyethylene-naphthalate, fluorinated polymers, polyester, silicone, polyurethane, or vinyl; paper; foils; medical foam; thermoplastic polyurethane (TPU), heat-fusion TPU, rubber and combinations thereof.

3. The electrode array of claim 1, wherein said measurement electrodes are spaced substantially evenly around said C-shaped portion.

4. The electrode array of claim 1, wherein said plurality of electrodes and said conductive traces comprise electrically conductive ink on said flexible substrate.

5. The electrode array of claim 4, wherein said electrically conductive ink is selected from the group consisting of silver (Ag) ink, silver-silver chloride (Ag—AgCl) ink, poly(3,4-ethylenedioxythiophene) polystyrene sulfonate (PEDOT:PSS), conductive graphene or carbon based ink, and combinations thereof.

6. The electrode array of claim 1, further comprising a dielectric or insulating material on said flexible substrate over said conductive traces.

7. The electrode array of claim 1, wherein said flexible substrate further comprises an adhesive deposited to promote adhesion between said flexible substrate and a human face during use.

8. A method of performing an electro-oculogram comprising:
    providing an electrode array comprising:
        a flexible substrate formed from a non-electrically conductive material, said flexible substrate comprising a C-shaped portion and a connector portion;
        a plurality of electrodes at predetermined locations on said C-shaped portion, said plurality of electrodes comprising a set of measurement electrodes, at least one ground electrode and a reference electrode; and
        a plurality of conductive traces connecting said plurality of electrodes to said connector portion;
    attaching said electrode array to a human face such that said C-shaped portion substantially circumscribes a human eye orbit and said measurement electrodes contact said human face; and
    connecting said plurality of electrodes to an electrical potential reading device via said conductive traces, said at least one ground electrode providing a common electrical ground of 0 Volts and said measurement electrodes being measured against said reference electrode.

9. The method of claim 8, wherein said attaching is performed by using adhesive backing on said flexible substrate.

10. The method of claim 8, further comprising flexing or deforming said flexible substrate to conform said electrode array to said human face by opening further or closing in said C-shaped portion.

11. The method of claim 8, wherein said plurality of electrodes comprises:
    a set of at least 3 substantially evenly spaced electrodes placed above the eyebrow on a top portion of said C-shaped portion;
    a set of at least 3 substantially evenly spaced electrodes placed below the eye on a bottom portion of said C-shaped portion;
    a set of at least 3 substantially evenly spaced electrodes placed to the side of the eye opposite the nose on a vertical portion of said C-shaped portion; and
    a set of 2 electrodes, each placed at the terminal portions of the C-shaped portion.

12. The method of claim 8, further comprising applying a conductive liquid or gel at a cavity of said measurement electrodes to lower impedance between said measurement electrodes and said human face.

* * * * *